United States Patent [19]

Antonuk et al.

[11] Patent Number: 5,079,426

[45] Date of Patent: Jan. 7, 1992

[54] MULTI-ELEMENT-AMORPHOUS-SILICON-DETECTOR-ARRAY FOR REAL-TIME IMAGING AND DOSIMETRY OF MEGAVOLTAGE PHOTONS AND DIAGNOSTIC X RAYS

[75] Inventors: Larry E. Antonuk, Ann Arbor, Mich.; Robert A. Street, Palo Alto, Calif.

[73] Assignees: The Regents of the University of Michigan, Ann Arbor, Mich.; Xerox Corporation, Palo Alto, Calif.

[21] Appl. No.: 681,650

[22] Filed: Apr. 8, 1991

Related U.S. Application Data

[63] Continuation of Ser. No. 403,450, Sep. 6, 1989, abandoned.

[51] Int. Cl.⁵ .............................................. G01T 1/24
[52] U.S. Cl. ........................... 250/370.09; 250/370.11; 250/370.14
[58] Field of Search ............... 250/370.14, 370.09, 250/370.11, 211 J; 357/2

[56] References Cited

U.S. PATENT DOCUMENTS

| | | | |
|---|---|---|---|
| 4,146,904 | 3/1979 | Baertsch et al. | 250/370.11 |
| 4,382,187 | 5/1983 | Fraleux et al. | 250/211 J |
| 4,589,003 | 5/1986 | Yamada et al. | 357/2 |
| 4,752,814 | 6/1988 | Tuan | 357/2 |
| 4,785,186 | 11/1988 | Street et al. | 250/370.14 |
| 4,799,094 | 1/1989 | Rougeot | 357/2 |
| 4,810,881 | 3/1989 | Berger et al. | 250/370.09 |
| 4,823,178 | 4/1989 | Suda | 357/2 |
| 4,889,983 | 12/1989 | Numano et al. | 250/211 J |
| 4,940,901 | 7/1990 | Henry et al. | 250/370.09 |

FOREIGN PATENT DOCUMENTS 126583 5/1989 Japan ............................ 250/370.11

OTHER PUBLICATIONS

L. E. Antonuk et al., "Large Area Amorphous Silicon Photodiode Arrays for Radiotherapy and Diagnostic Imaging", pp. 1-12.

N. A. Baily et al., "Fluoroscopic Visualization of Megavoltage Therapeutic X Ray Beams", pp. 935-939.

P. Munro et al., "A Digital Fluoroscopic Imaging Device for Radiotherapy Localization", pp. 1-20, Oct. 9-14, 1988, New Orleans, La., Abstract #163.

Article entitled, "Hydrogenated Amorphous Silicon and Thin Film Electrons For Pixel Detectors", LBL-27844, 3 pages, Sep. 1989, V. Perez-Mendez et al.

Article entitled, "Amorphous Semiconductors For Particle Detection: Physical and Technical Limits and Possibilities", Nuc. Instr. & Methods in Phys. Research, A275, 1989, pp. 558-563, Bernard Equer et al.

Article entitled, "Amorphous Silicon Position-Sensitive Detector", Nucl. Instr. and Methods in Physics Research, A273, 1988, pp. 640-644, Koh-ichi Mochiki et al.

Perez-Mendez et al., "Proposed a-Si:H Electronics for Pixel Detector", Lawrence Berkeley Laboratory, LBL-26254, Nov. 1988.

Perez-Mendez et al., "The Application of Thick Hydrogenated Amorphous Silicon Layers to Charged Particle and X-Ray Detection", MRS, vol. 149, Apr. 1989, pp. 621-630.

Perez-Mendez et al., "Hydrogenated Amorphous Silicon Pixel Detectors for Minimum Ionizing Particles", Lawrence Berkeley Laboratory, LBL-25114, Apr. 1988.

Perez-Mendez et al., "Proposed Thin Film Electronics for a-Si:H Pixel Detectors", Lawrence Berkeley Laboratory, LBL-26254, Mar. 1989.

L. E. Antonuk et al., "Signal, Noise, and Readout Considerations in the Development of Amorphous Silicon Photodiode Arrays for Radiotherapy and Diagnostic X-Ray Imaging", SPIE Conference Medical Imaging V, Feb./Mar. 1991.

H. C. Tuan, "Amorphous Silicon Thin Film Transitor and Its Applications to Large-Area Electronics", Mat. Res. Soc. Symp. Proc., vol. 33, 1984, pp. 247-257.

Fujieda et al., "Applications of a-Si:H Radiation Detectors", LBL-27457, Jun. 1989.

Primary Examiner—Carolyn E. Fields
Attorney, Agent, or Firm—Oblon, Spivak, McClelland, Maier & Neustadt

[57] ABSTRACT

A multi-element-amorphous-silicon detector-array real-time imager and dosimeter for diagnostic or megavoltage X rays having megavoltage photons having a plurality of photodiodes made of hydrogenated amorphous silicon arrayed in columns and rows upon a glass substrate. Each photodiode is connected to a thin film field effect transistor also located upon the glass substrate. Upper and lower metal contacts are located below and above the photodiodes to provide the photodiodes with a reverse bias. The capacitance of each photodiode when multiplied by the resistance of the field effect transistor to which it is connected yields an RC time constant sufficiently small to allow real time imaging.

24 Claims, 2 Drawing Sheets

MULTI-ELEMENT-AMORPHOUS-SILICON-DETECTOR-ARRAY FOR REAL-TIME IMAGING AND DOSIMETRY OF MEGAVOLTAGE PHOTONS AND DIAGNOSTIC X RAYS

This application is a continuation of Ser. No. 403,450, filed Sept. 6, 1989, now abandoned.

BACKGROUND OF THE INVENTION

1. Field of the Invention

The present invention pertains generally to the field of radiation detecting devices and, more particularly, to the field of real-time radiation imaging devices.

2. Discussion of the Background

There are several instances in modern radiotherapy where real-time imaging of X rays is a highly useful and critically important technique.

In external beam megavoltage photon radiation therapy, it is highly desirable that the maximum dose be delivered to the target volume and the minimum dose be delivered to the surrounding tissue. Prior to treatment, which typically consists of irradiating the patient on a daily basis for several weeks, the patient undergoes a number of preparatory steps in order to identify the region to be irradiated and to determine a "treatment plan" specifying exactly how this irradiation is to be performed. Often, one of these steps is to place the patient on a "treatment simulator", which simulates the motions and geometry of the therapy machine, and which makes diagnostic quality fluoroscopic and radiographic x-ray images. The fluoroscopic imaging allows a real-time means of simultaneously observing patient anatomy and manipulating the position of the patient so as to achieve a desired patient orientation with respect to the simulated treatment beam. Unfortunately, current fluoroscopic devices use large cumbersome image-intensifier tubes which restrict the possible motions of the simulator, thereby limiting the treatment positions that can be simulated.

A permanent record of imaging information from the simulator is achieved by means of radiographic imaging with film as well as storage of the fluoroscopic images. These images are used to provide information which contributes to deciding what the target region should be and how the actual treatment is performed, i.e., what geometric and dosimetric combination of megavoltage beams to use to satisfactorily irradiate the target region but spare the surrounding normal tissues. Once a treatment plan has been determined, often with the assistance of a computer which allows, among other things, manipulation of the simulation information as well as CT or other imaging information, the patient is typically taken back to the simulator for a verification-simulation in order to verify the geometric correctness of the plan.

When the patient is brought into the treatment room, it is highly desirable, prior to treatment, to verify that the orientation of the patient with respect to the treatment beam closely coincides with the setup achieved in the simulator room. Once verified, the prescription dose can be delivered to the target volume and surrounding tissues. The achievement of this goal is complicated by the fact that the patient anatomy moves due to both voluntary and involuntary patient motions. Such complications encourage the possibility of delivering too little dose to the target region and/or overdosing the surrounding tissues. In addition, for treatment machines which use a computer-controlled scanning treatment beam, there is the additional uncertainty of whether the beam is correctly directed on a burst by burst basis.

The above problems can be overcome by real-time imaging. Several prototype real-time imagers are being developed around the world, but most have no practical applications to clinical use. A real-time clinical image detector has been developed by H. Meertens at the Netherlands Cancer Institute in Amsterdam which is disclosed in European Patent Application 0196138. The Meertens' device operates on the principle of a scanning liquid ionization chamber. However, the Meertens' device is able to detect only a small fraction of the imaging signal.

Radiation detecting devices are taught in Hynecek, U.S. Pat. No. 4,679,212; Luderer et al., U.S. Pat. No. 4,250,385; DiBianca, U.S. Pat. No. 4,707,608; Haque, U.S. Pat. No. 4,288,264; Kruger, U.S. Pat. No. Re. 32,164; Barnes, U.S. Pat. No. 4,626,688; and DiBianca et al., U.S. Pat. No. 4,525,628; however, these detectors do not make possible real-time imaging for megavoltage photons.

Imaging equipment has been developed based on the use of photostimulable phosphors wherein an image receptor plate coated with such phosphors is exposed to a radiation beam and then "read out" by means of laser stimulated luminescence with direct conversion of the light to digital form. However, this technology appears to offer no possibility of real-time imaging. Efforts to develop imagers based on camera-fluoroscopy combinations have produced images of greatly varying quality at rates ranging from two images a second to one image every eight seconds. However, such a camera's expensive and delicate imaging electronics would be irreversibly damaged after approximately 10-130 kilorads of dose. Thus, mirrors are used to reflect the light image produced by a metal-phosphor screen combination to a camera sitting outside of the direct radiation field. This makes necessary the presence of a bulky light box located in the vicinity of the treatment table where such obstructions are highly undesirable. Furthermore, with the camera's imaging surface 2 to 3 feet from the fluorescent screen, the solid angle subtended by the camera is small (less than 1%) and hence the image quality is limited by the light collection stage rather than by the available high-energy quanta.

Recently, an imager consisting of tightly packed, tapered, optical fibers has been reported. The fibers make up a $40 \times 40$ cm$^2$ surface, 12 cm thick, which sits in the beam behind a metal-fluorescence screen and "pipes" the light to a video camera. The optical fibers are bunched together in bundles of $1.5 \times 1.5$ cm$^2$ at the input end and the imager has a thickness of 12 cm. The optical fibers have to be bent to such an extent that light is lost due to the fact that the critical angle is exceeded. The system currently has a light collection efficiency no greater than that of the mirror-camera system and, like those systems, is rather bulky.

In the optical imaging systems discussed above, considerably less than 1% of the visible light photons emitted by the scintillating layer are converted into signal. As a direct consequence, the quantum sink is the light collection stage rather than the stage where X rays are converted to high-energy electrons which enter into the phosphor. Thus, the quality and speed of imaging in the above systems are adversely affected.

In selecting the materials for a real-time imager for megavoltage photon radiation therapy, care must be taken that the materials can withstand high levels of radiation exposure over long durations of time. Another consideration is that the radiation detecting elements be arranged over a relatively large surface area. For instance, a detection surface of at least 25×25 cm² is necessary for head and neck portals. For pelvic, abdominal and thoracic portals, a surface area of 50×50 cm² is desirable. Though solid state imagers are highly desirable, the manufacture of crystalline semiconductor detectors over such an area is certainly prohibitively expensive.

The development of a—Si:H (hydrogenated amorphous silicon) has resulted in the realization of a highly radiation resistant material which can be utilized over large surface areas at very economical cost. See V. Perez-Mendez, et al., "Signal, Recombination Effects and Noise in Amorphous Silicon Detectors", Nuclear Instrument and Methods in Physics Research A260 (1987) 195-200, Elsevier Science Publishers B. V.; and I. D. French et al., "The Effect of γ-Irradiation on Amorphous Silicon Field Effect Transistors", Applied Physics A31, 19-22, 1983, Springer-Verlag.

It is now realized that amorphous silicon thin film transistors have applications to large-area electronics, see H. C. Tuan, "Amorphous Silicon Thin Film Transistor and its Application to Large-Area Electronics," Mat. Res. Soc. Symp. Proc. Vol. 33 (1984) Elsevier Science Publishing Company, Inc.

Amorphous silicon ionizing particle detectors made of hydrogenated amorphous silicon are known which can detect the presence, position and amount of high energy ionizing particles, see Street et al, U.S. Pat. No. 4,785,186; however, the patent does not teach how a—Si:H photodiodes can be utilized in coordination with other elements to obtain a real-time imaging device.

Rougeot, U.S. Pat. No. 4,799,094, teaches a photosensitive device having an array of p-doped floating grids which connect with a substrate of lightly n-doped hydrogenated amorphous silicon. Since Rougeot uses transistors as light detectors, the quantity of electron-hole pairs generated would appear quite insufficient to realize real-time imaging.

SUMMARY OF THE INVENTION

Accordingly, one object of the present invention is to achieve a pulse-by-pulse monitoring of the centroid of a transmitted megavoltage radiation beam.

Another object is to obtain x-ray-like images of the patient for real-time portal localization and verification imaging using megavoltage beams.

Yet another object is to measure the transmitted dose of the radiation field.

A further object is to obtain real-time diagnostic quality images with a treatment simulator with far less restrictions of motion due to the presence of the imager.

These and other objects are achieved by providing a real-time imaging device for storing and retrieving an imaging signal resulting from megavoltage radiation bursts in radiation treatment machines or from a diagnostic x-ray generator. The real-time megavoltage imaging device has a conversion layer for converting photons from the megavoltage radiation bursts into electrons, a scintillation layer in which the electrons created in the conversion layer create visible light photons, and an upper electrode layer which is transparent and allows the visible light from the scintillation layer to pass through. A plurality of a—Si:H sensors is arranged in rows and columns to form a radiation detecting surface area. Each a—Si:H sensor is paired with a thin film field effect transistor. The RC time constant of the imaging device is calculated by multiplying the resistance of the transistor by the capacitance of the a—Si:H sensor.

The high energy electrons and visible light photons incident upon the sensors constitute an imaging signal. Sufficient amounts of this imaging signal can be detected, creating electron-hole pairs which are stored in the capacitance of the sensors. Thereafter this signal can be read out on a time scale determined by the RC time constant so that real-time imaging is made possible.

For the application of real-time imaging of a diagnostic x-ray beam, given that the interaction probabilities are considerably higher and the range of the electrons created by the photons much shorter, a single layer for diagnostic-energy photon conversion and creation of the light photons by the resulting electrons suffices.

In addition, given the thinness and uniformity of the amorphous silicon sensors and the substrates upon which they are deposited, it is furthermore possible to stack one imager upon another without significant degradation of the imaging information. For example, an array dedicated to determining the position of the scanning beam could be positioned under an array dedicated to imaging the megavoltage photon beam. Alternatively, an array dedicated to real-time diagnostic x-ray imaging could be positioned over an array dedicated to real-time megavoltage imaging. Such positioning would offer tremendous advantages to radiation therapy.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
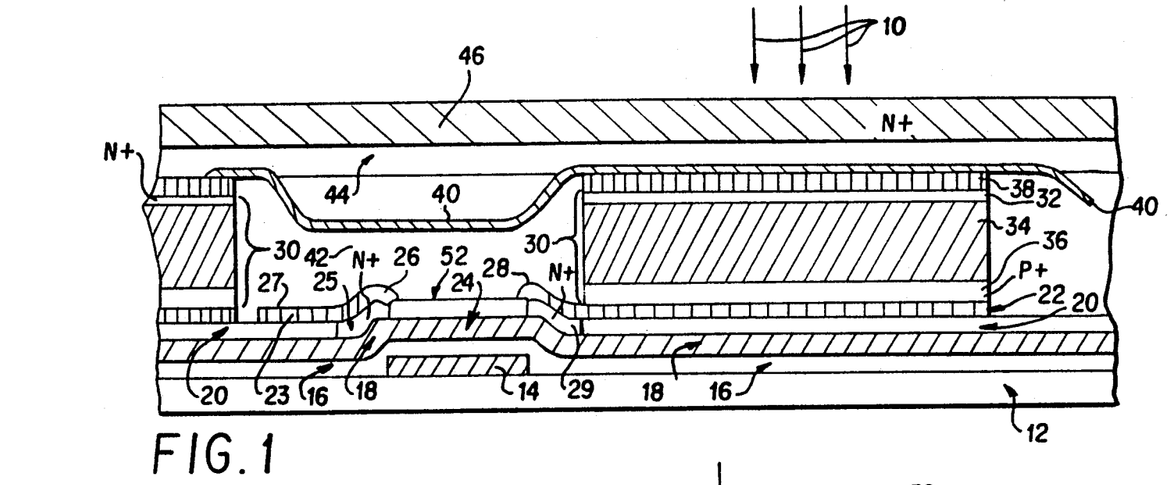
FIG. 1 is a cross-sectional side view of the present invention.

Referring now to the drawings, wherein like reference numerals designate identical or corresponding parts throughout the several views and, more particularly, to FIG. 1 thereof, a sensor 30 and thin-film field effect transistor 52 are shown mounted upon a glass substrate 12. The gate contact region 14 of the thin-film field effect transistor is seen to be positioned atop the glass substrate 12. Surrounding the gate contact region is a gate dielectric layer 16 of silicon nitride $Si_3N_4$ which also makes contact with the glass substrate 12. Above gate dielectric layer 14 is an a—Si:H layer 18.

Directly above the gate contact region 14 and making contact with the a—Si:H layer 18 is a second gate dielectric layer 24 made of silicon nitride. Adjacent to the sides of the lower portion of the second gate dielectric layer 24 are located n+ doped channel layers 25, 29 which are positioned so as to sandwich the lower portions of the second gate dielectric layer 24 therebetween. A drain contact region 26 and a source contact region 28 are positioned so as to sandwich the upper portion of the second gate dielectric layer 24 between them. These structured layers above and to the side of the gate contact region constitute a thin-film field effect transistor 52. Alternatively, microcrystalline silicon thin-film-transistors can be implemented to achieve faster read-out-speed.

This thin-film field effect transistor 52 is connected to a sensor 30 which constitutes a p-i-n photodiode. The sensor 30 is connected to the source contact region 28 of the thin-film field effect transistor 52 by means of lower electrode layer 22.

Above lower electrode layer 22 is p+ doped a—Si:H layer 36, layer 36 being approximately 400 Å thick. Above layer 36 is an intrinsic a—Si:H layer 34 which is at least one micron thick and preferably being approximately 3 microns or more thick for reasons which will be subsequently discussed. Above the intrinsic layer 34 is an n+ doped layer of a—Si:H 32, which is approximately 100 Å thick.

Above n+ doped layer 32 lies the upper electrode 38 which is made of a material transparent to visible light. A material such as indium tin oxide (ITO) is a suitable material for the upper electrode 38. A scintillating layer 44 for purposes of converting electrons to visible light is located directly above and preferably makes contact with the transparent upper electrode 38. Scintillating layer 44 may be a CRONEX TM scintillating screen made by Dupont, a LANEX TM scintillating screen made by Kodak or other suitable material.

For megavoltage beams, a photon-to-electron conversion layer 46 is located directly above and makes contact with scintillating layer 44. Conversion layer 46 is a 1 millimeter thick copper sheet; however, the thickness can be varied depending on the energy level of the radiation to which it is exposed. A 1 mm thick copper sheet when combined with a CRONEX TM scintillating screen and exposed to a megavoltage (~3-50 MV) photon beam produces pulses of light for about 10 microseconds. A 1 mm thick copper sheet when combined with a LANEX TM scintillating screen produces pulses of light for about 1 millisecond when exposed to a megavoltage beam.

Optionally, a suitable phosphor material may be deposited directly onto the sensors or onto the photon-to-electron converter in order to optimize the spatial resolution of the imager. For diagnostic imaging, the interaction of X rays with the scintillation layer 44 is such that the conversion layer 46 is not necessary.

As is shown in FIG. 1, polyimide 42 is placed over the field effect transistor 52 and between sensors 30 to provide insulation.

Figure 2:
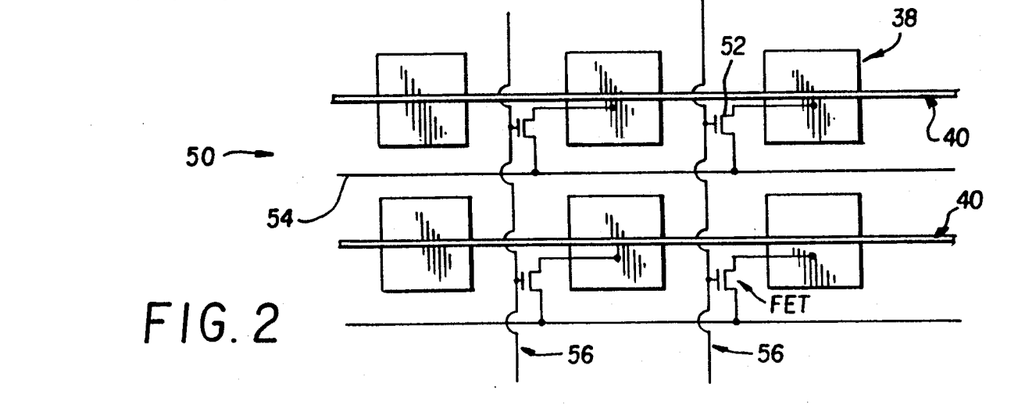
FIG. 2 is a top view illustrating the array of sensors and transistors.

FIG. 2 shows an array of sensors 50 according to the present invention. Biasing lines 40 are seen to connect the sensors 30 by being connected across the upper electrode layer 38 of each sensor in a given row. As will be appreciated by those skilled in the art, a metal layer (not shown), e.g. of aluminum, is coincident with those regions of biasing lines 40 which are located between the sensors 30. Such a metal layer serves to shield the transistors 52 from light. Signal lines 54 are shown to connect to the drain of each field effect transistor 52 in a given row.

From FIG. 1 it can be seen that a drain electrode layer 23 extends away from a side of drain contact region 26. Metallization (not shown) extends vertically downward from the end 27 of the drain electrode layer 23 away from transistor 52. This metallization is constructed to connect with a signal line 54 which lies on the substrate 12 in front of the sensor 30. Gate select lines 56 (FIG. 2) are seen to connect the gates of the thin-film field effect transistors located in a given column.

Thus, the sensors and thin-film field effect transistors are arranged in rows and columns so as to form an array 50 mounted upon a glass substrate 12 and form a detection panel.

A 25.6×25.6 cm² imaging panel is made of approximately 65,536 or more individual sensors. A typical imaging panel will have a 256×256 array of sensors or more. Each sensor is approximately 0.9 millimeters long or smaller with a density of at least 1 sensor per square millimeter being desired. Four panels of the 25.6×25.6 cm² sensor arrays can be combined to form a roughly 50×50 cm² surface so that the invention can be utilized for virtually any imaging function.

Figure 4:
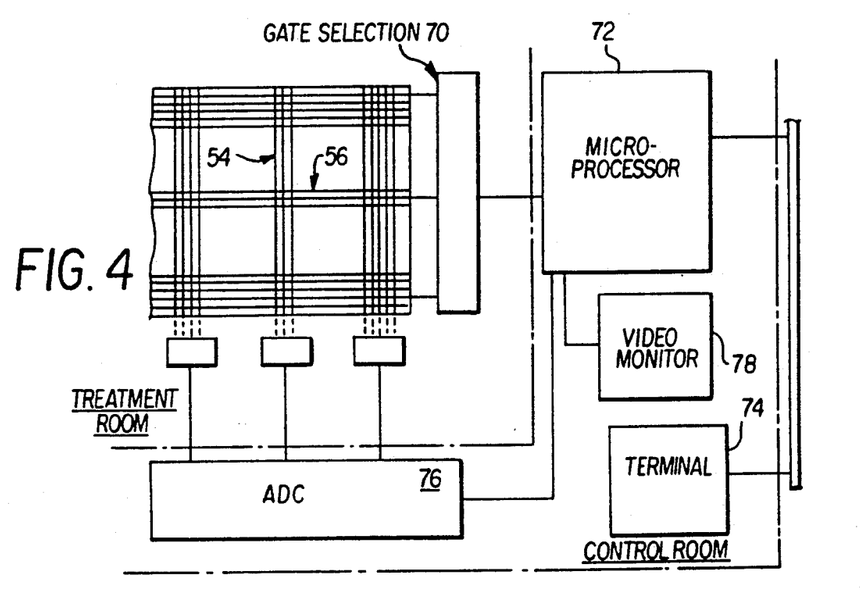
FIG. 4 is a schematic block diagram illustrating interfacing of sensors and transistors with known support electronics.

FIG. 4 shows the layout of the read-out electronics. Each gate select line 56 is addressed sequentially with a shift register. The signal lines 54 are connected to an amplifier and switching electronics. Either a charge or voltage amplifier may be used. If it is the latter, then a capacitor is included on the array at each signal line. The charge or voltage is sensed just after the end of each gate pulse, after which the signal line is reset to ground potential before the next gate pulse.

As shown in FIG. 1, a radiation beam 10 is directed upon the photon-to-electron conversion layer 46 which converts the photons of the radiation beam to electrons, some of whose energy is absorbed in scintillating layer 44 and thereby converted to visible light. This visible light passes through the transparent upper electrode 38 and into the sensor 30 where electron-hole pairs are generated in the intrinsic layer 34. The present invention allows 70 to 95 percent of the visible light photons emitted from scintillating layer 44 to be converted to electron-hole pairs in the sensors. The sensor 30 has a capacitive effect when a reverse bias is applied to all of the sensors by means of the biasing lines 40. This reverse bias causes the electron-hole pairs to be attracted to the upper and lower electrodes 38 and 22 where the signal generated from the radiation bursts are thus stored.

The thicker the intrinsic layer 34 is, the greater the ionization caused by the incident high energy and visible light radiation. However, as the thickness of layer 34 increases, the applied bias must increase proportionally in order to ensure that the electron-hole pairs generated throughout the intrinsic layer are efficiently collected and positioned at the upper and lower electrodes. A thickness of 1 micron is sufficient to absorb all the visible light from the phosphor. The choice of thickness is determined in part by the capacitance requirements of the sensor.

The size of the signals stored by the capacitance of the sensors constitutes the information from which the images are produced. The speed at which the size of these signals may be sampled is characterized by a time constant, RC, which is given by the product of the sensor capacitance and the on-resistance of the transistor. In general, it is highly desirable to design the sensors and transistors so that this RC time constant is as small as possible since the contribution of noise to the signal, collected by interfacing electronics located off of the array, will be minimized when the sampling period is as short as possible. A second constraint upon the sampling period for certain applications of radiation therapy is the requirement that the array be capable of being read out after every burst of radiation. This latter constraint demands that the RC time constant be less than the time interval between radiation pulses divided by the number of columns in the array. The former considerations of noise would encourage even further reductions.

The inverse of the on resistance of the transistor at a gate voltage $V_G$, is given by:

$$1/R = (W/L)\mu FE(V_G - V_T)C_G$$

where W and L are the width and length of the transistor, $\mu FE$ ($\sim 0.5$ cm$^2$/Vsec) is the carrier mobility, $V_T$ (=1V) is the threshold voltage and $C_g$ ($\sim 10^{-8}$ F/cm$^2$) is the gate capacitance. Typically, W/L is 10-100 so that $R \sim 0.1$-1 Mohm. If the sensor capacitance is 50 pF, then the RC time constant can be as small as 5 microseconds, thus satisfying the speed requirements.

At present, a column of sensors can be read out approximately every 10 microseconds. Therefore to read 256 columns would take 2.56 milliseconds. If the interval between radiation bursts is set at 2.56 milliseconds, this would give sufficient time to read out 256 columns in between radiation bursts. Thus, the time interval between radiation bursts, if set at 2.56 milliseconds, when divided by 256 rows would yield a time of 10 microseconds. Since the signal decays in an exponential fashion, the majority of the signal information is obtained during one time constant. Therefore, for this example, the desired time constant for the imaging device would be less than 10 microseconds.

The capacitance of each sensor and the resistance of each transistor should be designed so that the product of their respective capacitances and resistances is equal to the time constant desired. With the signal information stored in the sensor being adequately sampled during a time scale determined by the time constant, real time imaging is made possible.

The intrinsic layer 34 must be at least 1 micron thick or greater for purposes of converting and collecting photons over virtually the entire visible spectrum. As the intrinsic layer increases in thickness, capacitance diminishes and the ionization signal from high energy quanta increases. Furthermore, as the aspect ratio (W/L) of the thin-film field effect transistor is increased, resistance is reduced. Thus, by widening the channel of the field effect transistor, an increase in the aspect ratio and consequently a decrease in resistance will be realized. Also, resistance can be reduced by increasing the bias received by the gate of the field effect transistor.

Once the signal is stored in the sensors, obtaining the signal is relatively easy.

By applying a biasing voltage to the gate select lines the signal stored due to the capacitance of the sensor 30 is released from the source region to the drain region of the field effect transistor and is channeled through the signal lines 54 and on to interfacing electronics.

The ultimate limitation to the signal-to-noise ratio is the quantum noise of (i.e., statistical variations in) the number of high energy photons converting to high energy electrons which deposit energy in the phosphor, and an ideal detector will introduce no significant additional noise. For megavoltage beams, a typical gamma-ray burst will present approximately $5 \times 10^5$ photons/mm-size pixel, of which approximately 1% or $5 \times 10^3$ are converted into electrons producing visible light in the phosphor. This results because of absorption in the patient and loss in the copper/phosphor converter. A signal-to-noise ratio of 1000:1 requires $10^6$ of such converted photons for the quantum noise limit, and so requires approximately 200 bursts. Thus a high contrast image requires integration of the signal for 0.4-1 sec depending upon the dose rate and burst repetition frequency of the therapy machine. Such integration can be achieved either in the host computer or on the array. The inventors find that charge may be held in the array without significant loss for at least 1 second.

The converted gammas from a single burst yields approximately $10^7$ visible photons detected in each mm$^2$ sensor of the array. The quantum noise of this signal is dominated by that of the converted gammas. The measured noise in the read-out of a single element in the array is $10^4$-$10^5$ electrons. Therefore, no significant extra noise is introduced by the array, which will be capable of achieving the ultimate possible signal-to-noise ratio even when read out at every burst. Slower read out reduces even further the effect of read-out noise.

Figure 3:
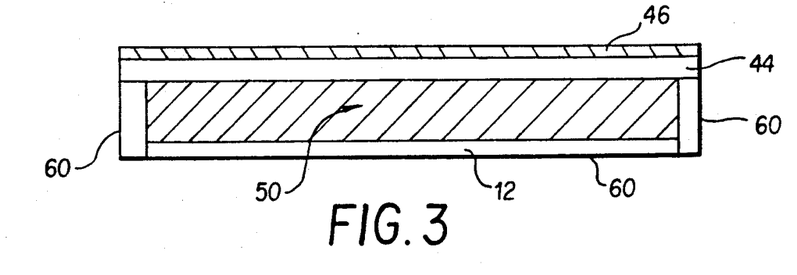
FIG. 3 is a cut away perspective side view of the sensor array enclosed in a shielded housing.

As it is essential that the sensors and their electronics be adequately shielded from stray electromagnetic radiation, including radio frequency and ionizing, FIG. 3 shows a shielded housing 60 made of copper in which a panel of sensors 50 is enclosed. In the case of megavoltage imaging, the top of the shielded housing 60 is seen to comprise the photon to electron conversion layer 46 and scintillating layer 44. In the case of diagnostic x-ray imaging, the top shielded housing is a layer which acts as both the converter and the scintillator. In the case where it is desirable to combine several such images, such as one for megavoltage imaging and another for burst-by-burst determination of the centroid of a scanning beam, the arrays for these imagers would be stacked inside of the shielded housing along with their photon-electron converters and scintillating screens.

FIG. 4 shows the array with known interfacing electronics. FIG. 4 serves to demonstrate how the gate select lines 56 can be activated by means of gate select electronics 70 connected to a microprocessor 72 which is connected to terminal 74. The signal lines 54 are seen to be interfaced with analog to digital converter 76 which is connected to microprocessor 72 and video monitor 78.

Figure 5:
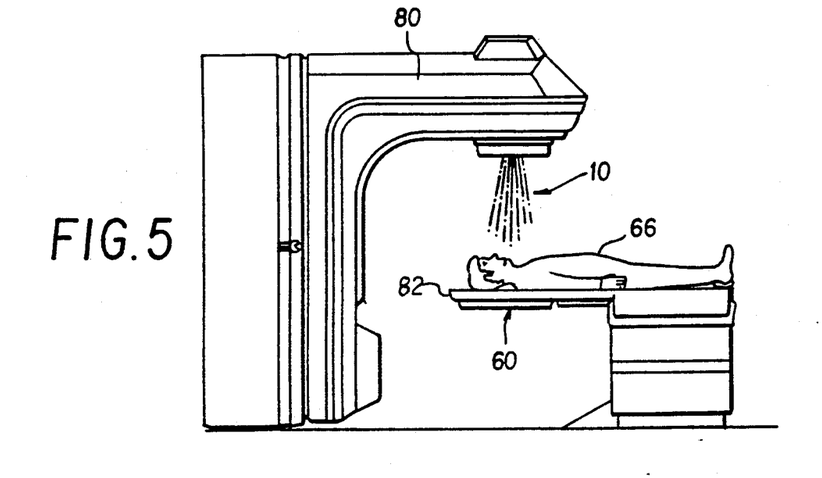
FIG. 5 is a general illustration showing how the present invention is utilized in a clinical setting.

FIG. 5 shows a radiation machine 80 and a patient 66 lying on table 82 receiving treatment from the radiation beam 10. The shielded housing 60 enclosing the array of sensors 50 is seen to lie below the patient underneath table 82. The arrangement would be similar in the case of a diagnostic imager located in the simulator room.

The discussion which follows is intended to give the reader a firm understanding of what the term "real-time" means in regard to the present invention.

If the invention is to be used for determining the centroid of a scanning megavoltage beam on a pulse-by-pulse basis then real-time operation requires that a very large fraction, preferably all, of the sensors be read out between bursts. This mode of operation is desirable with a scanning megavoltage beam machine. Such a machine typically has a variable pulse repetition rate ranging from 60 to 500 hertz. Thus, there are 2 to 16.7 milliseconds between bursts. The speed at which a given row from the array must be read out to satisfy this real-time requirement will depend upon the number of rows per array and the pulse repetition rate.

If the invention is to be used for imaging the megavoltage therapy beam, then there are two distinct modes, localization and verification imaging, in which real-time operation is required. In the case of localization imaging, just prior to the treatment, it is desired to give the patient a small fraction of his daily dose adequate to provide sufficient high energy photons to form an image. In this case, the signals stored in the sensors would be allowed to accumulate until the termination of the irradiation, at which time the sensors would be read out. The state of knowledge of the megavoltage beams indicates that acceptable images should be possible with the invention after periods of 0.1 seconds to several seconds depending upon the imaging situation and desired contrast. Real-time imaging would certainly be achieved in this instance if the final picture were available within several seconds or less after irradiation. As has been explained, it is essential that each column of sensors be read out as quickly as possible.

In a second real-time imaging situation, it is desirable to produce images one after the other during the course of a treatment. Given that the treatment may last ~10 to 60 seconds and given that there is imaging information after 0.1 seconds to several seconds, real-time operation in this case demands that the imager be read out as quickly as possible after sufficient information has accumulated in the sensors.

In the case of radiographic imaging, as in localization imaging, the goal is to irradiate the patient sufficiently so as to produce a high quality image. The present invention achieves real-time operation by allowing a final picture to be available in several seconds or less.

With regards to the RC time constant, the invention has been designed so that the columns of sensors can be read out as quickly as possible. This is a consequence of the fact that the external electronics which sample the signals from the sensors also sample noise from various sources, and this noise contribution increases with increasing sampling periods. Hence, it is highly desirable to keep this noise to a minimum by reducing the period during which the charge on the sensors is sampled. As has been mentioned, a major determinant of the speed at which this sampling can occur is given by the capacitance of the sensor times the on-resistance of the thin-film-transistor. Thus, by keeping the RC time constant to a minimum, the present invention achieves real-time imaging with a superior signal-to-noise ratio.

The present invention makes possible the detection of the centroid of the megavoltage radiation beam as many times per second as there are radiation bursts and the determination of the transmitted radiation dose on a burst by burst basis. Further, the present invention verifies the radiation dose is directed upon the desired target area. The present invention achieves a superior signal-to-noise ratio and receives enough information for an image to be formed in 1/10 of a second, (10 images a second), the only limitation being the speed of the processing hardware.

The present invention may be used for years at a time without a degradation in performance due to continued exposure to megavoltage radiation. When there is some radiation damage to the array, a simple heat treatment at 130°-150° C. restores the original characteristics of the device.

The present invention allows the replacement of the bulky image intensifier tube with a thin imaging system whose profile offers minimal obstruction to the motions of the simulator.

Finally, the present invention allows the creation of combinations of imagers which are stacked one on top of the other. The various imagers in the stack may be optimized for various forms of imaging.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A real-time imaging device, said device being for use with an incident radiation beam, said device comprising:
conversion means for converting said radiation beam to visible light;
signal detection means including an a—Si:H sensor having a predetermined capacitance for detecting the visible light and for storing a signal corresponding to the detected light; and
switching means including a transistor having a predetermined resistance for reading out the signal stored by said signal detection means, wherein the capacitance of the a—Si:H sensor when multiplied by the resistance of the transistor yield an RC time constant which is less than 10 microseconds, thereby to permit real-time imaging of said radiation beam.

2. A device according to claim 1, further comprising:
means for generating a megavoltage radiation beam as said incident radiation beam.

3. A device according to claim 2, wherein a plurality of a—Si:H sensors and a plurality of transistors are arrayed in rows and columns.

4. A device according to claim 3, wherein the plurality of transistors are thin film field effect transistors.

5. A device according to claim 1 further comprising:
bias means for applying a reverse bias to said a—Si:H sensor.

6. A real-time imaging device for storing and retrieving an imaging signal resulting from incident radiation bursts, comprising:
a scintillation layer;
an a—Si:H sensor having a first a—Si:H layer doped to a first conductivity type, a second a—Si:H layer doped to a second conductivity type, and an intrinsic a—Si:H layer sandwiched between said first and second a—Si:H layers; and
a transistor having a predetermined resistance connected to a a—Si:H sensor for reading out the stored signal, wherein the capacitance of the a—Si:H sensor when multiplied by the resistance of the transistor yield an RC time constant less than 10 microseconds, thereby to permit real-time imaging of said incident radiation bursts.

7. A device according to claim 6 further comprising:
bias means for applying a reverse bias to said a—Si:H sensor.

8. A real-time imaging device according to claim 6 further comprising:
a conversion layer for converting photons from the radiation bursts into electrons, said scintillation layer converting the electrons created in the conversion layer to visible light, and means for generating megavoltage radiation bursts as said incident radiation bursts.

9. A device according to claim 6, wherein:
the transistor is a thin film field effect transistor.

10. A device according to claim 9, further comprising:
an upper electrode layer transparent to the visible light so as to allow the visible light from the scintillation layer to pass therethrough;
a lower electrode layer; and wherein
the a—Si:H sensor is located between the upper and lower electrode layers.

11. A device according to claim 10, wherein said thin film field effect transistor comprises:
a gate contact region;
a gate dielectric layer placed over the gate contact region;
an a—Si:H layer placed over the gate dielectric layer;
a second gate dielectric layer located directly above the gate contact region and connected to a a—Si:H layer;
a first doped a—Si:H channel region and a second doped a—Si:H channel region connected to selected layers of said a—Si:H layer, the lower portion of said second gate dielectric layer being sandwiched between said first and second doped a—Si:H channel regions;
a drain contact region;
a source contact region; and
the upper portion of said second gate dielectric layer being sandwiched between the drain contact region and the source contact region.

12. A device according to claim 11, wherein:
the source contact region is connected to the lower electrode layer.

13. A device according to claim 9, wherein a plurality of a—Si:H sensors and a plurality of thin film field effect transistors are arrayed in rows and columns.

14. A device for storing and retrieving an imaging signal obtained as a result of diagnostic X rays for purposes of realizing real-time images, comprising:
an array having a plurality of sensors arranged in rows and columns;
each sensor of said plurality of sensors being an a—Si:H sensor having a first a—Si:H layer doped to a first conductivity type, a second a—Si:H layer doped to a second conductivity type, and an intrinsic a—Si:H layer sandwiched between said first and second a—Si:H layers;
an upper electrode layer transparent to visible light connected atop said first a—Si:H layer of each of said sensors;
a lower electrode layer connected below said second a—Si:H layer of each of said sensors; and
a plurality of thin film field effect transistors each having a predetermined resistance, each transistor of said plurality of transistors being connected to and paired with a sensor of said plurality of sensors for reading out an imaging signal stored in a respective sensor upon irradiation by said diagnostic x-rays, wherein the capacitance of each a—Si:H sensor of said plurality of sensors when multiplied by the resistance of each transistor to which each a—Si:H sensor is connected yields an RC time constant less than 10 microseconds, thereby to permit real-time imaging of said diagnostic x-rays.

15. A device according to claim 14, wherein each thin film field effect transistor of said plurality of transistors comprises:
a gate contact region;
a gate dielectric layer placed over the gate contact region;
an a—Si:H layer placed over the gate dielectric layer;
a second gate dielectric layer located directly above the gate contact region and connected to the a—Si:H layer;
a first doped a—Si:H channel region and a second doped a—Si:H channel region connected to selected layers of said a—Si:H layer, the lower portion of said second gate dielectric layer being sandwiched between said first and second doped a—Si:H channel regions;
a drain contact region;
a source contact region; and
the upper portion of said second gate dielectric layer is sandwiched between said source and drain contact regions.

16. A device according to claim 15, wherein:
said lower electrode layer is connected to said source contact region.

17. A device according to claim 16, further comprising:
a biasing line located in a given row of the array and connected to the upper electrode layer atop the first a—Si:H layer of each sensor of said plurality of sensors in the given row.

18. A device according to claim 17, further comprising:
a signal line located in the given row of the array and connected to the drain of each thin-film field effect transistor of said plurality of transistors in the given row.

19. A device according to claim 18, further comprising:
a gate select line located in a given column of the array and connected to the gate of each thin-film field effect transistor of said plurality of transistors in the given column.

20. A device according to claim 19, further comprising:
a shielded housing enclosing said array of sensors.

21. A device according to claim 20, wherein:
the top of said shielded housing is comprised of a photon-to-electron conversion layer;
the bottom of the photon-to-electron conversion layer is connected to a scintillation layer which is connected to the upper electrode layer atop each sensor of said plurality of sensors.

22. A device according to claim 15 further comprising: bias means for applying a reverse bias to said a—Si:H sensor.

23. A real-time imaging device having a plurality of arrays one stacked upon the other, with each array of said plurality of arrays having a plurality of sensors arranged in rows and columns, each sensor of each array comprising:
a scintillation layer to convert incident radiation signals into visible light signal,
an a—Si:H sensor, said a—Si:H sensor having a first a—Si:H layer doped to a first conductivity type, a second a—Si:H layer doped to a second conductivity type, and an intrinsic a—Si:H layer sandwiched between said first and second a—Si:H layers;

a thin film field effect transistor connected to each a—Si:H sensor and formed upon a mutual substrate as said each a—Si:H sensor, for reading out a signal from said respective sensor, wherein a capacitance of each a—Si:H sensor of said plurality of sensors when multiplied by a resistance of each transistor to which each a—Si:H sensor is connected yields an RC time constant less than 10 microseconds, thereby to permit real-time imaging of said incident radiation signals.

24. A device according to claim 23 further comprising: bias means for applying a reverse bias to said a—Si:H sensor.

* * * * *

UNITED STATES PATENT AND TRADEMARK OFFICE
CERTIFICATE OF CORRECTION

PATENT NO. : 5,079,426
DATED : JANUARY 7, 1992
INVENTOR(S) : ANTONUK et al.

It is certified that error appears in the above-identified patent and that said Letters Patent is hereby corrected as shown below:

Column 7, line 12, change "on resistance" to --on-resistance--;

line 41, change "real time" to --real-time--.

Column 10, line 56, change "to a a-Si:H" to --to the a-Si:H--.

Column 11, line 22, change "to a a-Si:H" to --to the a-Si:H--.

Column 12, line 38, change "claim 18" to --claim 16--.

Signed and Sealed this

Third Day of August, 1993

Attest:

MICHAEL K. KIRK

Attesting Officer

Acting Commissioner of Patents and Trademarks